(12) United States Patent
Wickenhauser et al.

(10) Patent No.: US 8,623,334 B1
(45) Date of Patent: *Jan. 7, 2014

(54) TOPICAL ANESTHETIC

(76) Inventors: Alan J. Wickenhauser, Moro, IL (US); Stephen E. Peipert, Edwardsville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/608,068

(22) Filed: Sep. 10, 2012

Related U.S. Application Data

(63) Continuation-in-part of application No. 11/238,748, filed on Sep. 29, 2005, now Pat. No. 8,263,047.

(51) Int. Cl.
*A61K 8/00* (2006.01)
*A61K 8/33* (2006.01)
*A61K 8/37* (2006.01)
*A61K 8/41* (2006.01)
*A61Q 11/00* (2006.01)
*A61K 31/00* (2006.01)
*A61K 31/245* (2006.01)

(52) U.S. Cl.
USPC ............ 424/54; 514/535; 514/536; 514/781; 514/532; 424/49; 424/78.06

(58) Field of Classification Search
USPC ........... 424/49, 54, 78.06; 514/532, 535, 536, 514/781
See application file for complete search history.

(56) References Cited

U.S. PATENT DOCUMENTS

| | | | |
|---|---|---|---|
| 3,272,700 A | 9/1966 | Shupe | |
| 4,562,060 A | 12/1985 | Broberg et al. | |
| 4,713,243 A | 12/1987 | Schiraldi et al. | |
| 4,748,022 A | 5/1988 | Busciglio | |
| 4,981,693 A | 1/1991 | Higashi et al. | |
| 5,192,802 A | 3/1993 | Rencher | |
| 5,234,957 A | 8/1993 | Mantelle | |
| 5,276,032 A | 1/1994 | King et al. | |
| 5,413,792 A | 5/1995 | Ninomiya et al. | |
| 5,942,543 A | 8/1999 | Ernst | |
| 5,993,836 A | 11/1999 | Castillo | |
| 6,114,344 A | 9/2000 | Druzgala et al. | |
| 6,159,498 A | 12/2000 | Tapolsky et al. | |
| 6,299,902 B1 | 10/2001 | Jun et al. | |
| 6,413,499 B1 | 7/2002 | Clay | |
| 6,509,028 B2 | 1/2003 | Williams et al. | |
| 6,599,906 B1 | 7/2003 | Ku et al. | |
| 2003/0017133 A1 | 1/2003 | Abu-Izza et al. | |
| 2003/0027833 A1 | 2/2003 | Cleary et al. | |
| 2003/0124190 A1 | 7/2003 | Williams et al. | |
| 2005/0014823 A1 | 1/2005 | Soderlund et al. | |

FOREIGN PATENT DOCUMENTS

WO   02089849 A1   11/2002

OTHER PUBLICATIONS

PubMedID: 14996106; Br J Dermatol. Feb. 2004; 150(2):337-40.
PubMedID: 15762203; Dermatol Surg. Feb. 2005; 31(2):135-8.
PubMedID: 12436830; Dent Clin North Am. Oct. 2002; 46(4):759-66.
PubMedID: 14533061; Klin Monatsbl Augenheilkd. Sep. 2003; 220(9):625-8.
PubMedID: 15574604; Pediatrics. Dec. 2004; 114(6):e720-4.
PubMedID: 14533061; Br J Anaesth. Oct. 2003; 91(4):514-8.
2005 U.S. Pharmacopeia 28, National Formulary 23; pp. 1879-1884.
Johnson et al., JADA, vol. 106, Jan. 1983, pp. 53-56.
Meechan, John G., Dent Clin N Am (2002) 759-677.
Tulga et al., J Clin Pediatr Dent 23(3):217-220. 1999.
Speirs et al., British Dental Journal 2001; 190:444-449.
Miller, K.J. et al. Solubility and in vitro percutaneous absorption of tetracaine from solvents of propylene glycol and saline, International Journal of Pharmaceutics, 98(1993) 101-111.
Miller, K. J. et al. In vitro transdermal diffusional properties of tetracaine from a topical formulation, in Prediction of Percutaneous Penetration Proceedings, Apr. 1991, Scott, R.C. et al. (eds), IBC Technical Services, London.
Miller, K.J. et al. Importance of molecular aggregation in the development of a topical local anesthetic. Langmuir 1993, 9, 105-109.

*Primary Examiner* — Lezah Roberts
(74) *Attorney, Agent, or Firm* — Grace J. Fishel

(57) ABSTRACT

A topical anesthetic is provided containing about 3 wt % to 10 wt % tetracaine in a vehicle suitable for administration to the mucosa. The vehicle for transporting the tetracaine includes a water soluble mucoadhesive or a combination of mucoadhesives such as a high molecular weight poly(ethylene oxide) homopolymer and a cellulose polymer. The vehicle also includes propylene glycol. The tetracaine is ground into a powder and is suspended in a plasticized hydrocarbon gel which completes the vehicle.

5 Claims, 1 Drawing Sheet

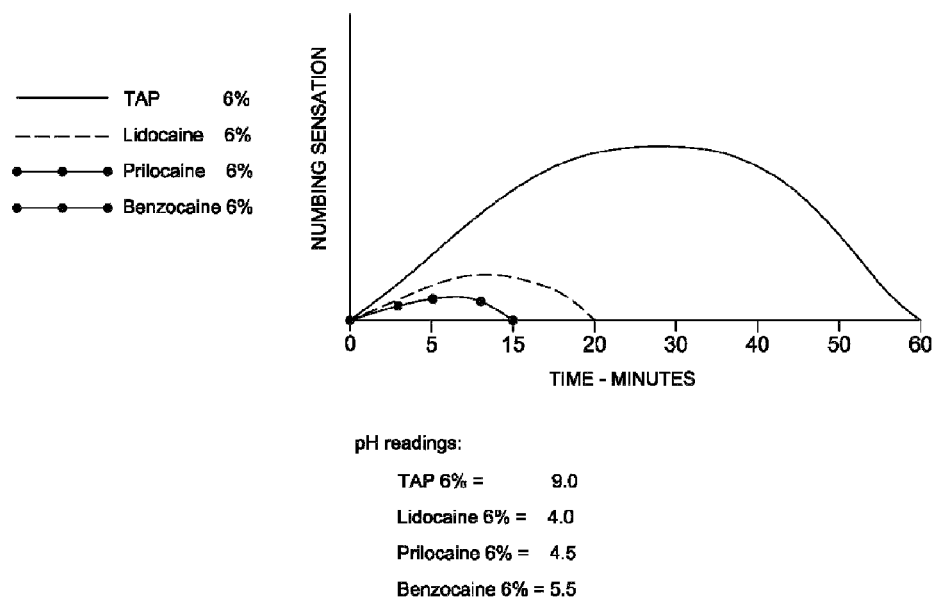

TOPICAL ANESTHETIC

This application is a continuation-in-part of U.S. application Ser. No. 11/238,748, filed Sep. 29, 2005, and issued as U.S. Pat. No. 8,263,047 on Sep. 11, 2012.

BACKGROUND OF THE INVENTION

1. Field of the Invention

The present invention relates to a topical anesthetic containing tetracaine as the sole anesthetic agent in a delivery vehicle suitable for administration to the skin, mouth, ear, nose, eye and other mucous membranes for the relief of pain.

2. Brief Description of the Prior Art

The literature is replete with references to tetracaine hydrochloride as an anesthetic agent frequently in combination with one or more other anesthetic agents, e.g., lidocaine, benzocaine, cocaine, etc. In modern practice, tetracaine's use has been restricted to topical anesthesia for ophthalmic procedures, amethocainelozenges for painful oropharyngeal conditions and as ametop for topical anesthesia of the skin in the form of tetracaine hydrochloride because tetracaine free base is not shelf stable. It is known that tetracaine free base fluxes across a biological membrane better than tetracaine hydrochloride but what has been lacking is a shelf stable formulation capable of delivering the tetracaine free base in active form.

BRIEF SUMMARY OF THE INVENTION

In view of the above, it is an object of the present invention to provide an effective topical anesthetic containing tetracaine free base. It is another object to provide a vehicle for delivering tetracaine with efficacy as a topical anesthetic. It is also an object to provide an essentially tasteless topical dental anesthetic that does not stimulate the production of saliva. Other objects and features of the invention will be in part apparent and in part pointed out hereinafter.

In accordance with the present invention, a topical anesthetic is provided containing about 3 wt % to 10 wt % tetracaine in a vehicle suitable for administration to the mucosa. The topical anesthetic binds to the mucosa and a sufficient amount of the tetracaine is transported into the mucosa in about three to five minutes to provide profound anesthesia at the application site. The anesthetic effect has a duration of about one to one and one-half hours. When used orally, the topical anesthetic improves subsequent injection comfort and may allow for other procedures to be performed without an injection.

The vehicle for transporting the tetracaine includes a water soluble mucoadhesive or a combination of mucoadhesives such as a high molecular weight poly(ethylene oxide) homopolymer and a cellulose polymer. The vehicle additionally includes propylene glycol which functions as penetration enhancer and is essential to (1) delivery of tetracaine free base in a stable form and (2) delivery at a pH which favors drug flux across the mucous membranes. The tetracaine is ground into a powder and is suspended in a plasticized hydrocarbon gel which completes the vehicle.

The invention summarized above comprises the compositions hereinafter described, the scope of the invention being indicated by the subjoined claims.

BRIEF DESCRIPTION OF THE DRAWINGS

In the accompanying drawings, FIG. 1 is a chart showing the efficacy and potency of several anesthetics in comparison to an anesthetic in accordance with the present invention.

DETAILED DESCRIPTION OF THE INVENTION

A topical anesthetic composition is provided for administration to the skin, eye, ear, nose, mouth and other mucous membranes to reduce pain or discomfort caused by minor skin irritations, cold sores or fever blisters, sunburn or other minor burns, insect bites or stings, poison ivy or oak rashes, and other sources of minor pain on a surface of the body. The topical anesthetic composition may be used to numb the skin or surfaces inside the mouth, nose and throat and to numb the surface of the eyes before a medical procedure. As compared to conventional topical anesthetics, the subject anesthetic composition has demonstrated improved efficacy, potency, convenience and duration when applied to the mucosa of a patient.

The tetracaine is provided in base form, i.e., not as the hydrochloride salt. Tetracaine is a white, or light yellow, waxy solid melting in the range of 41° to 46° C. It is very slightly soluble in water; soluble in alcohol, ether, benzene and chloroform. The amount of tetracaine in the formulation will vary depending on the desired therapeutic effect and duration of anesthesia needed.

In one embodiment of the of the present invention, the concentration of the tetracaine is from about 3 wt % to 10 wt % of the total composition to deliver an effective dosage. In another embodiment, the concentration of the tetracaine is from about 4 wt % to 8 wt % of the total composition. In yet another other embodiment, the concentration of the tetracaine is about 6 wt %.

One or more mucoadhesives is included in the composition. As used herein the term mucoadhesive means a natural or synthetic substance, e.g., gels, pastes, macromolecules, polymers, and oligomers, or mixtures thereof, that can adhere to a subject's mucous membrane for a period of time sufficient to locally deliver a therapeutically-effective amount of tetracaine. The composition itself need not be mucoadhesive, as long as it can form a mucoadhesive upon on the contact with the mucosa.

Examples of mucoadhesives for use in the present invention include, but are not limited to, pectin, alginic acid, chitosan, hyaluronic acid, polysorbates, such as polysorbate-20, -21, -40, -60, -61, -65, -80, -81, -85; poly(ethyleneglycol), such as PEG-7, -14, -16, -18, -55, -90, -100, -135, -180, -4, -240, -6, -8, -9, -10, -12, -20, or -32; oligosaccharides and polysaccharides, such as gellan, carrageenan, xanthan gum, gum arabic, and dextran; cellulose esters and cellulose ethers; modified cellulose polymers, such as carboxymethylcellulose, hydroxyethylcellulose, hydroxypropyl methylcellulose, hydroxyethyl ethylcellulose; polyether polymers and oligomers, such as polyoxyethylene; condensation products of poly(ethyleneoxide) with various reactive hydrogen containing compounds having long hydrophobic chains, condensation products of poly(ethylene oxide) with fatty acids, fatty alcohols, fatty amides, polyhydric alcohols; polyether compounds, such as poly(methyl vinyl ether), polyoxypropylene of less than 10 repeating units; polyether compounds, such as block copolymers of ethylene oxide and propylene oxide; ORABASE7 (i.e., a mixture of gelatine, pectin and sodium carboxymethyl cellulose in a plasticized hydrocarbon gel, commercially available from Hoyt laboratories, Needham, Mass.).

It is preferred that the mucoadhesive be water soluble and that a combination of mucoadhesives be used. Homopolymers of ethylene oxide are particularly preferred in combination with a second mucoadhesive such as sodium carboxymethylcellulose. Commercially available homopolymers of ethylene oxide are sold under the trademark POLYOX by Dow Chemical Company, Midland, Mich. POLYOX poly (ethylene oxide) polymers have a number of important properties for mucoadhesion—namely, water solubility, hydrophilicity, high molecular weight, hydrogen bonding functionality, and good biocompatibility. The polymers have a long linear chain structure which allows them to form a strong interpenetrating network with mucus. Data indicates that poly(ethylene oxide) polymers with a molecular weight of 4,000,000 and higher have the highest level of adhesion. The amount of mucoadhesive in the formulation depends upon the mucoadhesives selected and the consistency desired in the composition. One embodiment of the topical anesthetic composition makes use of POLYOX WSR 301 which has a molecular weight of 4,000,000 in combination with sodium carboxymethylcellulose medium viscosity. In this embodiment, the combined mucoadhesive makes up 10 wt % of the formula with POLYOX WSR 301 comprising about 3 wt % to about 8 wt % of the combination. In the absence of a mucoadhesive like POLYOX WSR 301, the topical adhesive tends to migrate from the site of application, spreading the numbing action of the tetracaine to unintended areas.

The topical anesthetic composition of the present invention includes propylene glycol as a penetration enhancer to increase the absorption of the tetracaine into the mucosa. Other suitable penetration enhancers may be included. The penetration enhancers should be physicochemically stable and not have pharmacologic effects and preferably should not have disagreeable smell, color or taste. In addition to propylene glycol, other glycols, monohydric alcohols, and fatty acid glycerides may also serve as penetration enhancers. The propylene glycol is present in the topical anesthetic composition in an amount from about 5 wt % to 15 wt %. When the poly (ethylene oxide) homopolymer is present in an amount of about 5 wt % and the sodium carboxymethylcellulose is present in an amount of about 4 wt %, it may be preferred that the propylene glycol be present in an amount of about 10 wt % as larger amounts of propylene glycol may render the paste too fluid to stay in place at the site of application.

A plasticized hydrocarbon gel completes the carrier vehicle for tetracaine in the topical anesthetic of the present invention. The plasticized hydrocarbon gel may be mixture of polyethylene in mineral oil. The plasticized hydrocarbon gel keeps the paste from dissolving away quickly, giving tetracaine time to penetrate. In one embodiment, the plasticized hydrocarbon gel makes up about 70 wt % of the formula.

The topical anesthetic compositions may include preservatives. Preferably, if present, the preservative comprises no more than about 1 wt %, but may vary depending on the other components.

The topical anesthetic compositions of the present invention may be prepared using ordinary production methods. In one embodiment, the composition is prepared as described in Example 1.

To relieve pain from dental procedures involving the gums or palate, the compositions of the invention are topically applied directly to the treatment area. The treatment area may be dried with a cotton swab and the composition then applied with a cotton applicator such as a Q-tip. It is not necessary to tightly control the dosage applied. If applied with a Q-tip, most operators will generally apply about 10 mg of paste. Less or more paste, for example from about 8 to 16 mg may be applied without toxic effect or raising an allergic reaction in most people. The larger amount may be needed to anesthetize the entire palate.

Unlike most common dental anesthetics, the anesthetic composition of the present invention has essentially no taste so there is no need to add a flavoring. The anesthetic composition tends to stay on the application site for effective absorption of the tetracaine, which effect occurs in about three to five minutes after application. There may be a synergistic effect between the delivery vehicle and the tetracaine as the anesthetic effect (i.e., efficacy and potency of the tetracaine) is greater than was expected. Since the anesthetic composition has no flavor, it does not stimulate the flow of saliva which results in a drier field. Generally the treatment area does not need to be dried or rinsed prior to or after injection (if injection is needed).

The anesthetic composition improves injection comfort and allows for other procedures to be performed without the use of what typically requires an injection of Novocain. Procedures such as scaling and root planing, gross debridement, Tofflimiere application, and tissue retained extractions may be performed without use of infiltration of any kind. The anesthetic composition has also been used without infiltration during crown or bridge procedures on teeth which have gone through root canal therapy, whether in the maxillary or mandibular region.

For use in reliving minor pain on a surface of the body, the smallest amount of the anesthetic composition needed to numb the skin or relieve the pain should be applied.

The following examples 1-9 illustrate the invention or are provided for purposes of comparison therewith.

Example 1

A composition of the present invention is described in Table 1 below.

TABLE 1

| Ingredient | Amount | Weight Percent |
| --- | --- | --- |
| Tetracaine | 1.8 g | 6 |
| Propylene Glycol | 3.0 ml | 10 |
| Sodium Carboxymethyl cellulose USP Medium Viscosity | 1.2 g | 4 |
| POLYOX WSR 301 | 1.5 g | 5 |
| Plastibase | 22.5 g | qs |

Sodium carboxymethyl cellulose in an amount of 1.2 g, 1.5 g of POLYOX WSR 301 and 2.0 g of tetracaine were ground in separate glass mortars to a fine powder and set aside. Ten percent extra tetracaine was weighed out because some of the tetracaine adhered to the mortar. By starting with 10% extra, the ground tetracaine available for transfer resulted in a 6 wt % composition.

Plastibase in an amount of 11.25 g was placed in a 200 ml beaker and the beaker placed directly onto a hotplate. The temperature of the hot plate was set on its lowest position. The Plastibase was gently heated until it became soft and semi-fluid. At which point, the Plastibase was workable for compounding purposes. Plastibase melts at about 82° F. Heating was stopped before the Plastibase totally melted as separation occurs and Plastibase will not resume its original consistency when cooled.

The ground sodium carboxymethylcellulose was added in small portions to the heated Plastibase with stirring after each addition to ensure a uniform mix. The beaker was removed from the heat and the mixture cooled.

On an ointment slab, 1.8 g of the finely ground tetracaine was worked with 0.75 ml of propylene glycol (25% of the total propylene glycol specified in Table 1). The tetracaine and propylene glycol mixture was combined with 11.25 g of Plastibase via geometric dilution. The cooled Plastibase and sodium carboxymethylcellulose mixture was then worked into the tetracaine, propylene glycol and Plastibase mixture via geometric dilution.

In a glass mortar the ground POLYOX WSR 301 was wetted with 2.25 ml of propylene glycol (75% of the total propylene glycol specified in Table 1).

The POLYOX WSR 301 and propylene glycol mixture was then incorporated via geometric dilution with the other ingredients previously mixed together on the ointment slab to form 30 g of topical anesthetic paste.

The topical anesthetic paste prepared as described above was then placed in ointment jars and refrigerated. Under refrigeration, the topical anesthetic paste was still effective after six months.

Example 2

Several healthy volunteers were recruited from members of a professional dental staff. Approximately 10 mg of paste as prepared in Example 1 was applied to the muco-buccal fold in the maxillary molar region of each subject with a cotton applicator following drying of the mucosa.

All of the subjects reported profound anesthesia at the application site which persisted for approximately 1 to 1½ hours depending on the subject's metabolism and level of physical activity.

Example 3

Prior to infiltration with an injectable anesthetic, approximately 10 mg of topical anesthetic from Example 1 was applied with a Q-tip to the site of injection. The topical anesthetic was rubbed over the mucosa for approximately 10 seconds. The Q-tip was then removed and three to five minutes allowed to lapse before Novocain was injected with a needle.

The subjects reported that they felt no pain upon injection and no taste was perceived. Saliva production was not stimulated and the field remained dry.

Some practitioners have observed that less injectable anesthetic was required to achieve complete anesthesia.

Example 4

Approximately 10 mg of paste as prepared in Example 1 was applied to the buccal and to the lingual or to the buccal and to the palatal sides of a tooth prior to removing a crown or bridge. When the tooth had previously received root canal therapy, no injection was required and the patients reported no discomfort in preparing the tooth for a new crown or bridge. When benzocaine 20 wt % was used as the topical anesthetic, most patients required an injection.

Example 5

When approximately 10 mg of paste as prepared in Example 1 was applied to the buccal side and 16 mg of paste was applied to the palate, dental scaling and root planing of the maxilla dentition in pockets up to 6-7 mm was accomplished without a palatal injection being needed.

In the past, a palatal injection was usually made before attempting scaling and root planing. Painful palatal injection was thus avoided by applying the subject topical anesthetic.

Patients with pockets deeper than about 7 mm are generally referred to a periodontist.

Example 6

Fear of syringes and needle insertions is very common among children and a bad dental experience may have a negative impact on the child's willingness to attend to dental care in the future. In pediatric patients, tissue retained extractions of the primary dentition have been accomplished without injection by application of 10 mg of paste as prepared in Example 1 to the tissue supporting the tooth.

Example 7

A topical anesthetic was prepared with benzocaine 20 wt % in the vehicle described in Example 1. When the anesthetic was applied as described in Example 2, the subjects reported that the anesthetic effect was not as pronounced as with commercially available benzocaine 20 wt % in gel form. A topical anesthetic was also prepared with 3 wt % lidocaine in the vehicle described in Example 1. When applied as described in Example 2, the subjects reported that the anesthetic effect was better than with 20 wt % benzocaine in the vehicle but that the taste was bitter. In addition, the anesthetic effect only lasted about 10 to 15 minutes which is not enough for many dental procedures.

Example 8

A sample of TAP 6% identified as batch 080608 was prepared as described in Example 1.
The formula was as follows:

| Ingredient | Weight Percent |
| --- | --- |
| Tetracaine Free Base | 6 |
| Propylene Glycol | 10 |
| Sodium Carboxymethyl Cellulose USP Medium Viscosity | 4 |
| POLYOX WSR 301 | 5 |
| Plastibase | qs |

The product was stored in a refrigerator for approximately 25 months and subjected to HPLC-mass spectrometry analysis. The results showed that 94.9% of the extracted drug was present as intact tetracaine and 5.1% as the propylene glycol transester. There was no propylene glycol diester noted in the sample.

Other than with the vehicle described herein, tetracaine free base when used at all is usually mixed with lidocaine and epinephrine. Commercially available combinations of such anesthetics when refrigerated have a shelf life of 150 days.

Example 9

To demonstrate the effect of removal of the supportive elements of the vehicle Example 1 was repeated as follows:
(a) Removed the Sodium Carboxymethyl Cellulose keeping the other ingredients the same. The product was less tactile to the mucosa, slumping was observed, pH was 9.0.
(b) Removed the POLYOX WSR 301. The product was much thinner in consistency and dropped off an applicator, pH was 9.0.
(c) Removed the Plastibase. The powders settled out and the product was not useful in a clinical setting, pH not recorded.

Example 10

To demonstrate that the vehicle described in Example 1 does not have the same effect on the efficacy and potency of other anesthetics as it does tetracaine free base, 6 weight % Lidocaine, 6 weight % Prilocalne and 6 weight % Benzocaine, respectively, were substituted for 6 weight % tetracaine free base. Each of the formulas was applied to the oral mucosa and the time that numbing was experienced recorded. The results are as shown in the following chart:

In view of the above, it will be seen that the several objects of the invention are achieved and other advantageous results attained. As various changes could be made in the above compositions without departing from the scope of the invention, it is intended that all matter contained in the above description or shown in the accompanying drawings shall be interpreted as illustrative and not in a limiting sense.

What is claimed:

1. A topical anesthetic for use in producing local anesthesia in about three to five minutes when applied to skin or mucosa, said topical anesthetic comprising tetracaine free base in an amount from about 4 wt % to about 8 wt % of the topical anesthetic in a non-aqueous vehicle, wherein the non-aqueous vehicle comprises a high molecular weight poly(ethylene oxide) homopolymer in combination with a cellulose polymer wherein the combination makes up about 10 wt % of the topical anesthetic, said high molecular weight poly(ethylene oxide) homopolymer is present in an amount from about 3 wt % to about 8 wt % of the combination; propylene glycol in an amount from about 5 wt % to 15 wt % of the topical anesthetic; and a plasticized hydrocarbon gel in an amount of about 70 wt % of the topical anesthetic, said topical anesthetic being stable under refrigeration for at least twenty-five months as to efficacy and potency of the tetracaine free base as an anesthetic.

2. The topical anesthetic of claim 1 wherein the poly(ethylene oxide) homopolymer has a molecular weight about 4,000,000 daltons.

3. The topical anesthetic of claim 1 wherein the poly(ethylene oxide) is present in an amount of about 5 wt % and the cellulose polymer is sodium carboxymethylcellulose and is present in an amount of about 4 wt % of the combination.

4. The topical anesthetic of claim 3 wherein the propylene glycol is present in an amount of about 10 wt %.

5. The topical anesthetic of claim 4 having a consistency of a paste and an anesthetic duration of about one to one and one-half hours.

* * * * *